NEW AND DISTINCT VARIETY OF GLADIOLUS
Filed Nov. 19, 1971
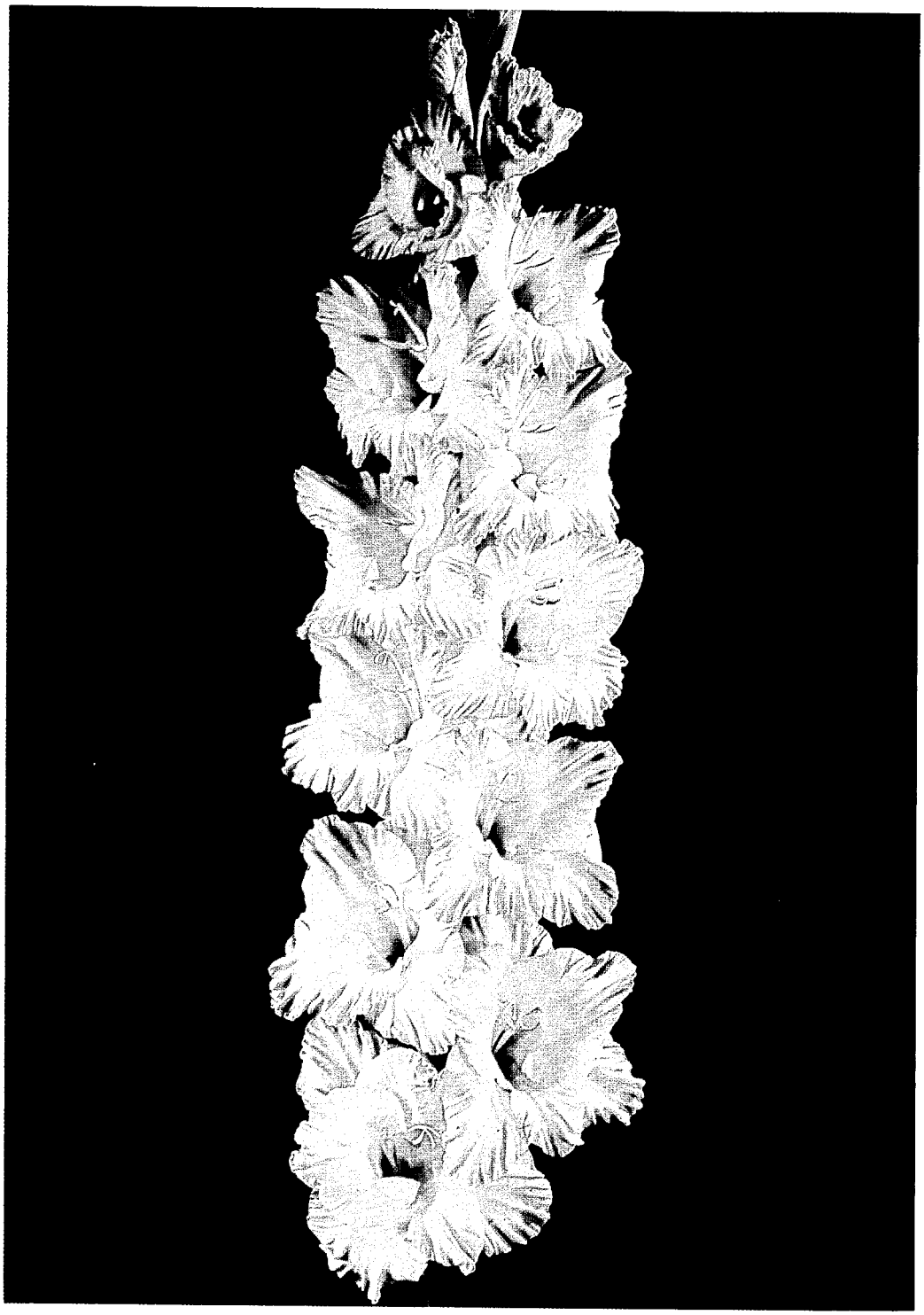

United States Patent Office

Plant Pat. 3,461
Patented Jan. 29, 1974

3,461
GLADIOLUS PLANT

John R. Larus, West Hartford, and Charles T. Larus, Avon, Conn., assignors to Selected Glads, Inc., New Albany, Ind.

Filed Nov. 19, 1971, Ser. No. 200,623
Int. Cl. A01h 5/00
U.S. Cl. Plt.—85 1 Claim This invention relates to a new and distinct variety of gladiolus plant.

This new gladiolus plant was originated by us by crossing the variety known as "Ben Hur" with the variety known as "Party Ruffles × Landmark," "Ben Hur" being the seed parent, "Party Ruffles × Landmark" being the pollen parent, "Ben Hur" and "Landmark" being patented, the Landmark seedling being registered with the North America Gladiolus Registry, published in Sandina, N.Y.

The improved variety resulting from this breeding is evidenced by the following unique combination of characteristics which are outstanding therein and which distinguish our new variety from its parents, as well as from other varieties of which we are aware:

First: Pure deep pink color with no visible foreign color.
Second: The ability to open up to 12 florets at one time.

In addition to these major characteristics our variety is also endowed with the following characteristics:

(1) Unusual and lavish ruffing
(2) High bud count
(3) Stem freedom from crooking
(4) Large exhibition type spikes
(5) Good health
(6) Admirable and consistent growth habits
(7) Excellent propagative powers
(8) Very formal, regular placement in perfect double rows.

We have asexually reproduced the new variety by natural increase from cormels through several generations in Connecticut, and succeeding generations have established that the distinguishing characteristics of the variety held true through propagations by plantings derived from cormels.

The accompanying drawing shows a typical specimen of a flower spike of the new variety, with the flowers in varied stages of growth. Some are shown as partially opened buds and others as fully opened buds. The colors depicted are as nearly true as is possible to achieve in this type of reproduction.

The following is a detailed description of our new variety, with color terminology in accordance with the Horticultural Color Charts issued by the British Color Council and the Royal Horticultural Society, except where general color terms of ordinary dictionary significance are obvious.

PLANT

Growth: Vigorous and healthy; excellent propagator.

Blooming habit: Comes into bloom, under normal conditions, in approximately 80 days, in northeastern latitudes of the United States, after planting.

Stems:
*Form.*—Exceptionally straight.
*Diameter at base.*—About ¾ inch.
*Color at base.*—Purple base of steam just above bulb.

Foliage: Above the ground they are medium green. The leaves of this variety are of a slightly lighter green shade than most varieties. The average leaf is one and one-half inches wide at the base, grows forty inches long, tapers gracefully to a point and droops artistically from the spot where the taper begins, about twentyfour inches from the ground. Stem of flowerhead has light green cast and sheaths are a darker green.

Disease resistance: The variety has been found to be unusually resistant to the usual gladiolus plant diseases of a bacterial, viral or fungoid genesis.

Corms: Mature bulbs are round and moderately crowned with waved husks which have light tan cast.
*Color of flesh.*—Light yellow.

FLOWER

Spike:
*Form and size.*—Straight and fairly tall with bloom spike 55 to 60 inches in height and regularly carrying 18 to 21 buds with flowerhead ranging 24 to 30 inches long.

Bud:
*Size.*—About 3 inches long when opening.
*Opening.*—On first blooming 3 or 4 buds open with 2 or 3 a day opening thereafter.

Flower:
*Arrangement.*—Flowerhead of the new variety has an extremely formal placement wherein all florets face forward in two rows.
*Size.*—Individual florets average about 4½ inches in diameter.
*Form.*—Florets have triangularly arranged outside petals and offset triangularly arranged inside petals, all of which are unusually ruffled.
*Keeping qualities.*—The flowers are long lasting.

Petals:
*Shape.*—Oval with slight notch at points.
*Size.*—Upper petals—about 1½ inches wide. Lip petals—about 1⅛ inches wide.
*Aspect.*—Florets face up slightly when partially open, and face straight out when fully open. Petals are ruffled at edges to about one-third of the way toward the base.
*Fragrance.*—None.
*Color.*—Medium rose pink at petal edges and light rose pink on upper petal. Medium rose ring at base of petals, and small white throat with pale light rose blotch. Ruffled pink—Plate 0621 with Empire rose shading to 0621/3 in upper throat.

REPRODUCTIVE ORGANS

Stamens:
*Color.*—White with deep blue lines.

Pistils:
*Color.*—White coming out of calyx and pale rose white where stamens and pistil develop.

GROWTH

Locality where grown and observed: West Hartford, Conn.

Propagation: Holds its distinguishing characteristics through succeeding propagations from cormels.

It can be seen that this variety is unique in the precision with which the deep pink florets open, up to twelve at a time, and in the ruffling along the edges of the florets.

What we claim is:

1. A new and distinct variety of gladiolus plant, substantially as herein shown and described, characterized particularly as to novelty by the unique combination of its deep pink color, and its ability to open up to twelve florets at a time.

No references cited.

ROBERT E. BAGWILL, Primary Examiner